United States Patent
Cohen et al.

(10) Patent No.: US 11,031,118 B2
(45) Date of Patent: Jun. 8, 2021

(54) MIXED ELECTROANATOMICAL MAP COLORING TOOL HAVING DRAGGABLE GEODESIC OVERLAY

(71) Applicant: BIOSENSE WEBSTER (ISRAEL) LTD., Yokneam (IL)

(72) Inventors: Assaf Cohen, Kiryat Bialik (IL); Itai Doron, Katsir (IL); Amiram Sheiner, Zichron Yaakov (IL); Illya Shtirberg, Nesher (IL); Assaf Govari, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/537,658

(22) Filed: Aug. 12, 2019

(65) Prior Publication Data
US 2021/0050091 A1 Feb. 18, 2021

(51) Int. Cl.
*G06F 3/0484* (2013.01)
*G16H 30/00* (2018.01)
*A61B 34/10* (2016.01)
*A61B 5/339* (2021.01)
*A61B 5/00* (2006.01)
(Continued)

(52) U.S. Cl.
CPC ............. *G16H 30/00* (2018.01); *A61B 5/339* (2021.01); *A61B 5/7475* (2013.01); *A61B 34/10* (2016.02); *G06F 3/04845* (2013.01); *G06T 3/0068* (2013.01); *A61B 2034/105* (2016.02); *A61B 2090/364* (2016.02); *G06T 2200/24* (2013.01)

(58) Field of Classification Search
CPC ...... G06F 3/04845; G06F 2203/04805; G16H 30/00; A61B 34/10
See application file for complete search history.

(56) References Cited

U.S. PATENT DOCUMENTS 5,672,877 A * 9/1997 Liebig ................. A61B 6/5235
250/363.04
5,818,455 A * 10/1998 Stone .................... G06T 3/0018
345/619
(Continued)

FOREIGN PATENT DOCUMENTS

KR 2015115438 A 10/2015

OTHER PUBLICATIONS

European Search Report for corresponding EPA No. 20190531.2 dated Dec. 23, 2020.
(Continued)

*Primary Examiner* — Dino Kujundzic
(74) *Attorney, Agent, or Firm* — Dergosits & Noah LLP; Todd A. Noah

(57) ABSTRACT

A method includes receiving two or more surface representations of at least a portion of an organ of a patient. The two or more received surface representations are registered one with the other. One of the surface representations is selected as a base map. A draggable geodesic region is generated for at least one of the two or more surface representations not selected as a base map, wherein the geodesic region is configured to follow varying anatomy as the region is dragged over the base map. The draggable geodesic region is overlaid on the base map to generate a mixed multilayer representation, and the mixed multilayer representation is presented to a user.

14 Claims, 3 Drawing Sheets

(51) Int. Cl.
*G06T 3/00* (2006.01)
*A61B 90/00* (2016.01)

(56) References Cited

U.S. PATENT DOCUMENTS

| | | | | |
|---|---|---|---|---|
| 6,590,583 | B2* | 7/2003 | Soohoo | G06T 3/0018 |
| | | | | 345/660 |
| 8,456,182 | B2 | 6/2013 | Bar-Tal | |
| 8,799,799 | B1* | 8/2014 | Cervelli | G06T 11/60 |
| | | | | 715/765 |
| 9,189,852 | B2* | 11/2015 | Teittinen | G09G 5/14 |
| 10,019,819 | B2* | 7/2018 | Tripathi | G06K 9/4604 |
| 10,061,474 | B2* | 8/2018 | Bertoldo | G06F 3/0482 |
| 2003/0016850 | A1 | 1/2003 | Kaufman | |
| 2004/0125138 | A1* | 7/2004 | Jetha | G06F 3/0481 |
| | | | | 715/764 |
| 2006/0004275 | A1* | 1/2006 | Vija | G01T 1/1644 |
| | | | | 600/407 |
| 2006/0116575 | A1* | 6/2006 | Willis | A61B 5/743 |
| | | | | 600/434 |
| 2006/0133694 | A1* | 6/2006 | Dewaele | G06T 7/337 |
| | | | | 382/294 |
| 2006/0174209 | A1* | 8/2006 | Barros | G06F 3/0483 |
| | | | | 715/764 |
| 2007/0003119 | A1 | 1/2007 | Roehrig | |
| 2007/0299352 | A1* | 12/2007 | Harlev | A61B 5/6852 |
| | | | | 600/509 |
| 2008/0008401 | A1* | 1/2008 | Zhu | G16H 40/63 |
| | | | | 382/294 |
| 2010/0268059 | A1 | 10/2010 | Ryu | |
| 2012/0209108 | A1 | 8/2012 | Qian | |
| 2014/0015856 | A1* | 1/2014 | Xiao | A61B 5/0033 |
| | | | | 345/629 |
| 2014/0280180 | A1* | 9/2014 | Edecker | G06F 16/9535 |
| | | | | 707/740 |
| 2015/0339820 | A1 | 11/2015 | Santoro | |
| 2018/0325401 | A1* | 11/2018 | Stewart | A61B 18/1492 |
| 2019/0043197 | A1* | 2/2019 | Adler | G06T 17/10 |
| 2019/0151023 | A1* | 5/2019 | Lu | A61B 34/10 |

OTHER PUBLICATIONS

Etienne Delacretaz et al., "Multiple atrial macro-re-entry circuits in adults with repaired congenital heart disease: entrainment mapping combined with three-dimensional electroanatomic mapping", Journal of the American College of Cardiology, vol. 37, No. 6, May 1, 2001, pp. 1665-1676.

* cited by examiner

MIXED ELECTROANATOMICAL MAP COLORING TOOL HAVING DRAGGABLE GEODESIC OVERLAY

FIELD OF THE INVENTION

The present invention relates generally to cardiac mapping, and particularly to visualizing anatomical cardiac maps.

BACKGROUND OF THE INVENTION

Graphical tools for assisting the analysis of a rendered organ were previously proposed in the patent literature. For example, U.S. Patent Application Publication 2007/0003119 describes display and navigation methods for multiple computer-aided detection (CAD) detections. A medical image is displayed to a viewer, and a request is received to instantiate CAD-assisted viewing. A timewise presentation sequence for the CAD detections is automatically computed according to a predetermined sequencing criterion. For each CAD detection, an expanded presentation 2-dimensional window floating on a computer screen is displayed for its associated location in the medical image, the expanded presentation windows being displayed according to the timewise presentation sequence.

As another example, U.S. Patent Application Publication 2010/0268059 describes an exemplary method that includes accessing cardiac information acquired via a catheter located at various positions in a venous network of a heart of a patient. The cardiac information comprises position information, electrical information and mechanical information. Local electrical activation times are mapped to anatomic positions to generate an electrical activation time map. Local mechanical activation times are mapped to anatomic positions to generate a mechanical activation time map. An electromechanical delay map is generated by subtracting local electrical activation times from corresponding local mechanical activation times, and at least the electromechanical delay map is rendered to a display.

U.S. Patent Application Publication 2003/0016850 describes systems and graphical user interfaces for analyzing body images. In an exemplary embodiment, the invention provides a graphical user interface having a display coupled to a micro processing device and a memory device. The graphical user interface has an electronic representation of a first body image and a second body image and an electronic map representing the position of nodules on the first body image and second body image. In an embodiment, a result in image is derived by a binary operation between two input images.

SUMMARY OF THE INVENTION

The present invention provides a method, including receiving two or more surface representations of at least a portion of an organ of a patient and overlaying them. The two or more received surface representations are registered one with the other. One of the surface representations is selected as a base map. A draggable geodesic region is generated for at least one of the two or more surface representations not selected as a base map, wherein the geodesic region is configured to follow varying anatomy as the region is dragged over the base map. The draggable geodesic region is overlaid on the base map to generate a mixed multilayer representation, and the mixed multilayer representation is presented to a user.

In some embodiments, the two or more surface representations include different types of electroanatomical (EA) maps.

In some embodiments, the different types of EA maps include color coded EA maps.

In another embodiment, the different types of EA maps include a bipolar map and a local activation time (LAT) map.

In some embodiments, the geodesic region has a circular shape. In other embodiments, the geodesic region is dragged in response to a user input.

In yet another embodiment, the method further includes, in response to the user input, selecting another surface representation as a base map, and generating the draggable geodesic region for at least one of the two or more surface representations not selected as a base map.

There is additionally provided, in accordance with an embodiment of the present invention, a system, including a memory and a processor. The memory is configured to store two or more surface representations of at least a portion of an organ of a patient. The processor is configured to (a) register the two or more received surface representations one with the other, (b) select one of the surface representations as a base map, (c) generate for at least one of the two or more surface representations not selected as a base map, a draggable geodesic region, wherein the geodesic region is configured to follow varying anatomy as the region is dragged over the base map, (d) overlay the draggable geodesic region on the base map to generate a mixed multilayer representation, and (e) present the mixed multilayer representation to a user.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
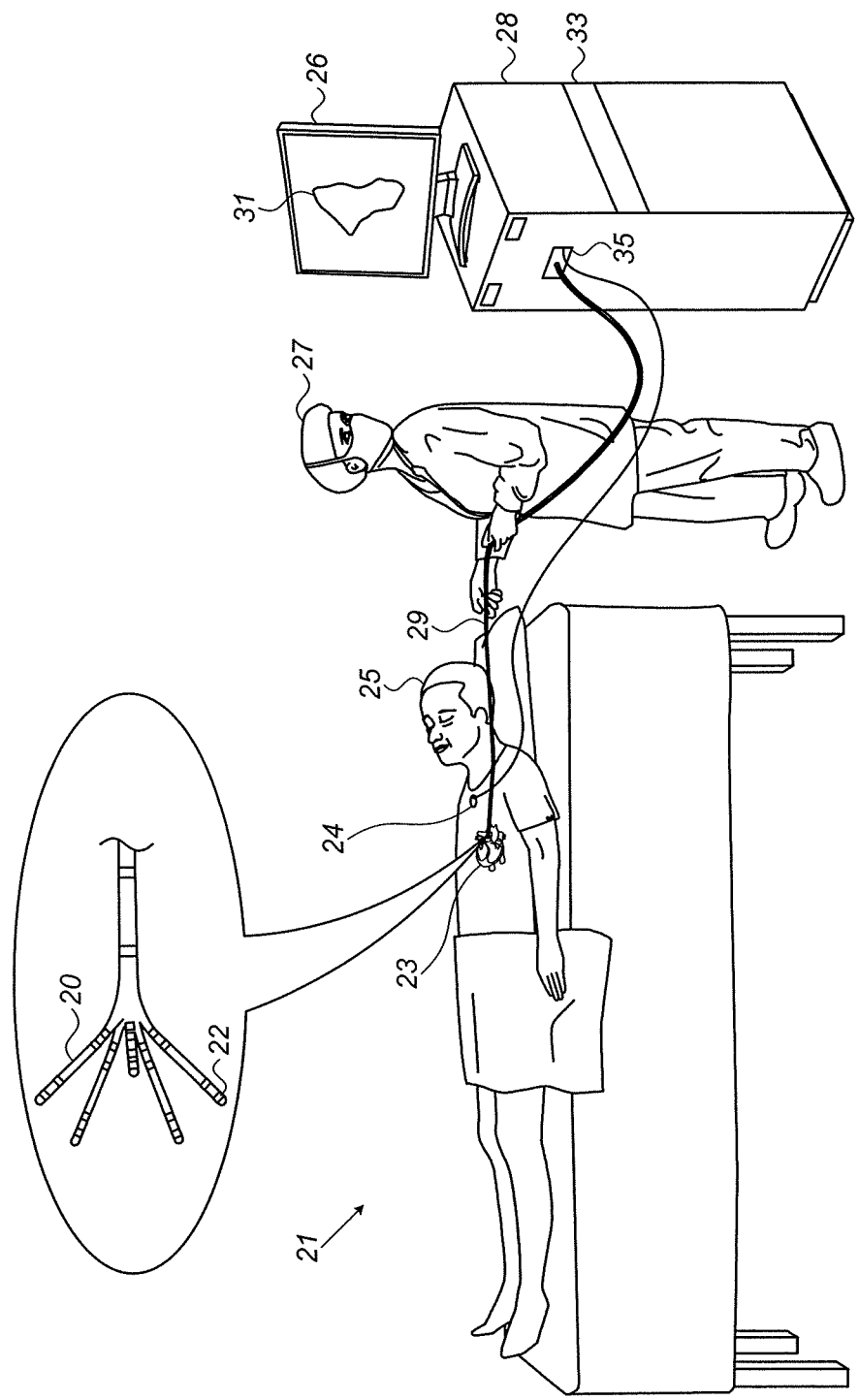
FIG. 1 is a schematic, pictorial illustration of a system for electroanatomical (EA) mapping, in accordance with an exemplary embodiment of the present invention.

Catheter-based electroanatomical (EA) mapping techniques may produce various types of EA maps of an organ, such as a left atrium of a heart. In some cases, to interpret the EA maps, a physician needs to compare two different EA maps. For example, to check for cardiac scar tissue, the physician may look at a local activation time (LAT) colored map and also at a bipolar potential colored map. The physician may toggle between the maps, or place them in two windows side-by-side. Either way is time consuming, and for both methods, because there is no registration, it is difficult to compare specific anatomical regions exactly.

Moreover, to facilitate clinical decisions, such as the amount of ablative energy to use at a region of the organ, the physician may need to visually examine other types of maps, for example, cardiac wall thickness and/or locations of major blood vessels in the region, further complicating the task of the physician.

Embodiments of the present invention that are described herein provide real-time and integrative mode methods for overlying one or more regions of surface representations, such as of EA maps or of other types of maps, on another surface representation, that may also be a type of an EA map.

In some exemplary embodiments, a processor registers two or more surface representations one with the other. Then, the processor selects one of the surface representations as a base map, based on user discretion or a prespecified protocol. The processor generates, for at least one of the two or more surface representations not selected as a base map, a draggable geodesic region, wherein the geodesic region is configured to follow varying anatomy as the region is dragged over the base map. The processor overlays the draggable geodesic region on one of the surface representations that serves as a base map. Finally, the processor presents a resulting mixed multilayer representation comprising the at least one draggable geodesic region to a user.

In an exemplary embodiment, the processor is further configured to provide a function, for example, to select another surface representation as a base map from a user interface tool, and to generate the draggable geodesic region for at least one of the two or more surface representations not selected as a base map.

In an optional exemplary embodiment, a variant of the disclosed method is provided in which the processor opens one or more windows, in one or more outer layers of the multiple layer representation, in order to view one or more inner layers therethrough. An opening of geodesic windows gives equivalent results as overlaying geodesic regions, by (i) reversing the order of maps, and (ii) opening geodesic windows in outer maps to view regions of the inner maps. In some exemplary embodiments of this invention, therefore, overlaying geodesic regions, or opening geodesic windows, are two means to achieve a similar user experience and similar benefits for the physician.

In an exemplary embodiment, the physician can move the geodesic region by dragging the geodesic region with a user interface tool, such as a computer mouse and/or touch screen.

In some exemplary embodiments, a processor overlays a circular geodesic region of a bipolar potential map on a LAT map. Using the user interface tool to drag and/or to change the size of the overlay, the physician can, for example, quickly check whether or not a cardiac tissue region is scarred, without the need to switch (i.e., to toggle) between the two EA maps.

In another exemplary embodiment, a LAT map may be overlaid in a geodesic region where the geodesic region has a different LAT range than the main map.

In another exemplary embodiment, the order of the EA maps may be exchanged (i.e., a geodesic region of the LAT map being overlaid on the bipolar potential map), by the physician toggling between two ordering options of the mixed map using, for example, the user interface tool. When multiple overlay regions of multiple maps are generated, the physician may reorder layers to select which layer would constitute a base map and which layers have regions overlaid on the base map.

In another exemplary embodiment, multiple geodesic regions may be opened simultaneously and independently placed and moved on the map.

Typically, the processor is programmed with a particular algorithm that enables the processor to conduct each of the processor-related steps and functions outlined above.

The disclosed techniques may assist the physician in the interpretation of two or more types of EA maps, as well as of other types of maps, of the same organ. The disclosed technique may thus expedite and improve the quality of complicated diagnostic tasks, such as those required in diagnostic catheterizations.

System Description

FIG. 1 is a schematic, pictorial illustration of a system for electroanatomical (EA) mapping, in accordance with an exemplary embodiment of the present invention. FIG. 1 depicts a physician 27 using an EA Pentaray® catheter 29 to perform an EA mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23. A processor 28 receives these signals via an electrical interface 35, and uses information contained in these signals to construct an EA map 31 that processor 28 stores in a memory 33. During and/or following the procedure, processor 28 may display EA map 31 on a display 26.

Figure 2:
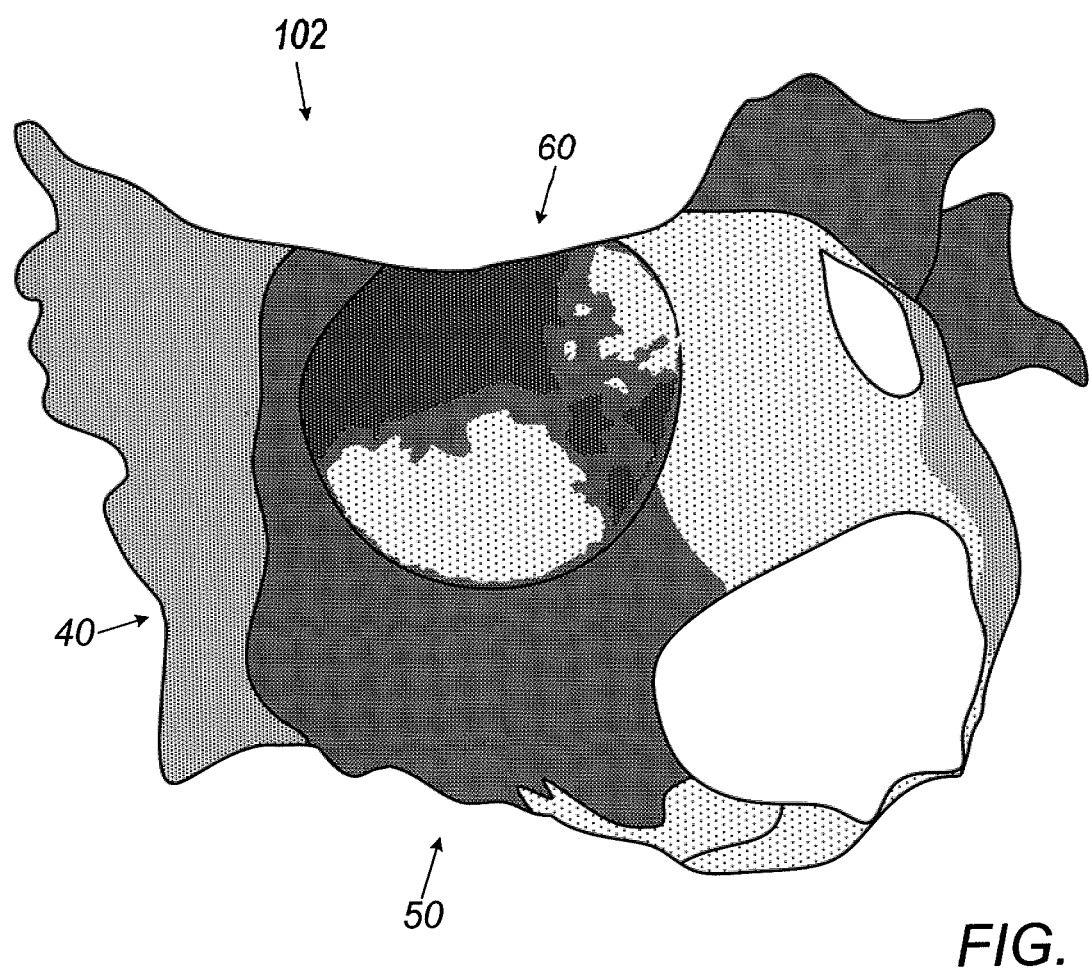
FIG. 2 is a schematic, pictorial volume rendering of a mixed electroanatomical (EA) map of a left atrium, in accordance with an exemplary embodiment of the present invention.

In some exemplary embodiments, EA map 31 comprises a circular geodesic overlay region of a bipolar potential map overlaid on a LAT map, as shown in FIG. 2 and described in detail subsequently.

During the procedure, a tracking system is used to track the respective locations of sensing-electrodes 22, such that each of the signals may be associated with the location at which the signal was acquired. For example, the Advanced Catheter Location (ACL) system, made by Biosense-Webster (Irvine Calif.), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface-electrodes 24, that are coupled to the skin of patient 25. For example, three surface-electrodes 24 may be coupled to the patient's chest, and another three surface-electrodes may be coupled to the patient's back. (For ease of illustration, only one surface-electrode is shown in FIG. 1.) Electric currents are passed between electrodes 22 inside heart 23 of the patient, and surface-electrodes 24. Processor 28 calculates an estimated location of all electrodes 22 within the patient's heart based on the ratios between the resulting current amplitudes measured at surface-electrodes 24 (or between the impedances implied by these amplitudes) and the known positions of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as ones based on measuring voltage signals. Other types of sensing catheters, such as the Lasso® Catheter (produced by Biosense Webster) may equivalently be employed. Contact sensors may be fitted at the distal end of EA catheter 29. As noted above, other types of electrodes, such as those used for ablation, may be utilized in a similar way, fitted to electrodes 22 for acquiring the needed position data. Thus, an ablation electrode used for collecting position data is regarded, in this case, as a sensing-electrode. In an optional embodiment, processor 28 is further configured to indicate the quality of physical contact between each of the electrodes 22 and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 3, that enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Mixed Electroanatomical Map Coloring Tool Having Draggable Geodesic Overlay

FIG. 2 is a schematic, pictorial volume rendering of a mixed electroanatomical (EA) map of a left atrium 40, in accordance with an exemplary embodiment of the present invention. As illustrated, FIG. 2 shows a draggable circular geodesic region 60 of a bipolar potential map overlaid on a LAT map 50. Geodesic region 60 shows color coded bipolar ECG signal amplitude, whereas LAT map 50 shows color-coded activation times (both shown herein in gray scale). The physician may move circular geodesic overlay region 60, for example, by dragging the inside of the circle, and also change the radius of circular region 60. Using the geodesic overlay, the physician can, for example, quickly check whether or not a cardiac tissue region is scarred without switching (i.e., toggling) between the two EA maps.

While FIG. 2 shows a circular geodesic overlay region, the overlaid region may have another shape, for example, one that provides an isometric view that varies with location over the organ. Furthermore, while FIG. 2 shows a mixed dual-layer EA map, the disclosed technique may overlay regions from more maps, so as to create a multilayer map that comprises two or more overlaid geodesic regions, of which at least one is not an EP map, such overlay region indicating, for example, cardiac wall thickness.

If maps are acquired at different times or using different location modalities, processor 28 may adjust one or more maps to best fit the current main map. In doing so, information from other maps will be properly displayed within the geodesic region of interest on the main map.

Figure 3:
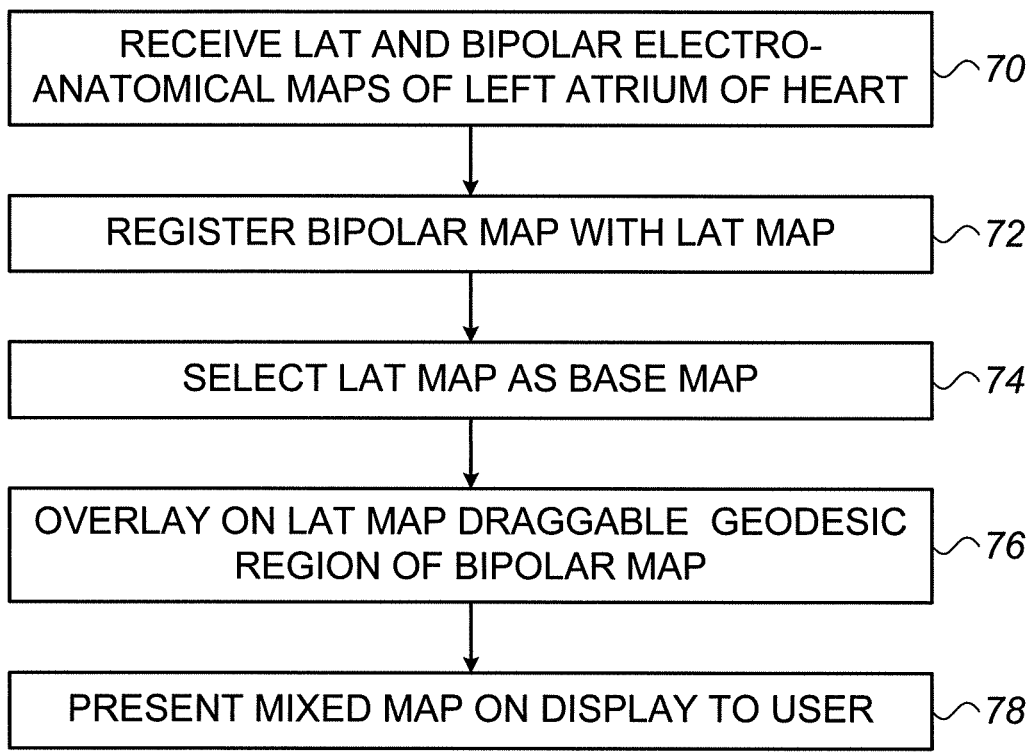
FIG. 3 is a flow chart that schematically illustrates a method for generating the mixed electroanatomical (EA) map of FIG. 2, in accordance with an exemplary embodiment of the present invention.

FIG. 3 is a flow chart that schematically illustrates a method for generating the mixed electroanatomical (EA) map of FIG. 2, in accordance with an exemplary embodiment of the present invention. The algorithm, according to the presented embodiment, carries out a process that begins with processor 28 receiving LAT and bipolar potential EA maps of left atrium 40, at a map-receiving step 70. In one exemplary embodiment, the processor uploads the maps from memory 33.

Next, processor 28 registers the bipolar map with the LAT map, at a map registration step 72.

Next, the processor selects LAT map 50 as a base map, at a base map selection step 74. Processor 28 generates a draggable geodesic region 60 of the bipolar potential map, and overlays region 60 on LAT map 50, at a region overlaying step 76. Finally, processor 28 presents the resulting mixed EA map 102 on a display to the physician, at a mixed map presenting step 78.

The exemplary flow chart shown in FIG. 3 is chosen purely for the sake of conceptual clarity. In optional exemplary embodiments, various additional steps may be performed, for example to automatically register additional layers, such as of medical images, and to generate and display respective geodesic overlay regions of the additional layers.

Although the embodiments described herein mainly address cardiac applications, the methods and systems described herein can also be used in other applications, such as in electroanatomical mapping of a brain or otolaryngology procedures, and with applications that display multiple layers of information on using 2D or RD graphics, such as multi modalities comprising CT\PET\MRI.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for cardiac mapping, comprising:
receiving two or more surface representations of at least a portion of an organ of a patient;
registering the two or more received surface representations one with the other;
selecting one of the surface representations as a base map, the base map comprising a first set of information;
generating for at least one of the two or more surface representations not selected as a base map, a draggable geodesic region, the draggable geodesic region comprising a second set of information, wherein the geodesic region is configured to move, wherein the second set of information is configured to change in response to the geodesic region being dragged over the base map;
overlaying the draggable geodesic region on the base map to generate a multilayer representation of the first set of information relating to the base map and the second set of information relating to the geodesic region; and
presenting the multilayer representation to a user.

2. The method according to claim 1, wherein the two or more surface representations comprise different types of electroanatomical (EA) maps.

3. The method according to claim 2, wherein the different types of EA maps comprise color coded EA maps.

4. The method according to claim 2, wherein the different types of EA maps comprise a bipolar map and a local activation time (LAT) map.

5. The method according to claim 1, wherein the geodesic region has a circular shape.

6. The method according to claim 1, wherein the geodesic region is dragged in response to a user input.

7. The method according to claim 6, and comprising, in response to the user input, selecting another surface representation as a base map, and generating the draggable geodesic region for at least one of the two or more surface representations not selected as a base map.

8. A system for cardiac mapping, comprising:
a memory, configured to store two or more surface representations of at least a portion of an organ of a patient; and
a processor, configured to:
- register the two or more received surface representations one with the other;
- select one of the surface representations as a base map, the base map comprising a first set of information;
- generate for at least one of the two or more surface representations not selected as a base map, a draggable geodesic region, the draggable geodesic region comprising a second set of information, wherein the geodesic region is configured to move, wherein the second set of information is configured to change in response to the geodesic region being dragged over the base map;
- overlay the draggable geodesic region on the base map to generate a multilayer representation of the first set of information relating to the base map and the second set of information relating to the geodesic region; and
- present the multilayer representation to a user.

9. The system according to claim 8, wherein the two or more surface representations comprise different types of electroanatomical (EA) maps.

10. The system according to claim 9, wherein the different types of EA maps comprise color coded EA maps.

11. The system according to claim 9, wherein the different types of EA maps comprise a bipolar map and a local activation time (LAT) map.

12. The system according to claim 8, wherein the geodesic region has a circular shape.

13. The system according to claim 8, wherein the geodesic region is dragged in response to a user input.

14. The system according to claim 13, wherein the processor is further configured to, in response to the user input, select another surface representation as a base map, and generate the draggable geodesic region for at least one of the two or more surface representations not selected as a base map.

* * * * *